(12) United States Patent
Tortelli et al.

(10) Patent No.: US 7,319,173 B2
(45) Date of Patent: *Jan. 15, 2008

(54) PROCESS FOR PREPARING FLUOROHALOGENETHERS

(75) Inventors: Vito Tortelli, Milan (IT); Stefano Millefanti, Como (IT); Pierangelo Calini, Milan (IT)

(73) Assignee: Solvay Solexis S.p.A., Milan (IT)

( * ) Notice: Subject to any disclaimer, the term of this patent is extended or adjusted under 35 U.S.C. 154(b) by 388 days.

This patent is subject to a terminal disclaimer.

(21) Appl. No.: 11/044,021

(22) Filed: Jan. 28, 2005

(65) Prior Publication Data

US 2007/0004940 A1    Jan. 4, 2007

(30) Foreign Application Priority Data

Jan. 29, 2004   (IT) ................. MI2004A0132

(51) Int. Cl.
*C07C 43/02* (2006.01)
*C07C 43/20* (2006.01)

(52) U.S. Cl. ............. 568/663; 568/669; 568/677; 568/684; 568/685; 560/849

(58) Field of Classification Search ............. 568/684, 568/685, 663, 669, 677; 560/849
See application file for complete search history.

(56) References Cited

U.S. PATENT DOCUMENTS

| | | | |
|---|---|---|---|
| 4,801,409 A | 1/1989 | Marraccini et al. | |
| 4,827,024 A | 5/1989 | Guglielmo et al. | |
| 4,900,872 A | 2/1990 | Guglielmo et al. | |
| 4,906,770 A | 3/1990 | Marchionni et al. | |
| 4,962,282 A | 10/1990 | Marraccini et al. | |
| 5,225,576 A | 7/1993 | Navarrini et al. | |
| 5,466,877 A | 11/1995 | Moore | |
| 5,756,814 A | 5/1998 | Lin et al. | |
| 6,835,856 B2 * | 12/2004 | Tortelli et al. | 568/615 |
| 7,019,177 B2 * | 3/2006 | Tortelli et al. | 568/615 |
| 7,157,600 B2 * | 1/2007 | Tortelli et al. | 562/825 |
| 2005/0171388 A1 * | 8/2005 | Tortelli et al. | 568/677 |

FOREIGN PATENT DOCUMENTS

| | | |
|---|---|---|
| DE | 195 37 997 A1 | 5/1996 |
| EP | 0 090 498 A2 | 10/1983 |
| EP | 0 133 020 A2 | 2/1985 |
| EP | 0 201 871 A1 | 11/1986 |
| EP | 0 269 933 A1 | 6/1988 |
| EP | 1 333 020 A2 | 8/2003 |
| EP | 1 388 531 A1 | 2/2004 |
| EP | 1 462 435 A1 | 9/2004 |

OTHER PUBLICATIONS

Krespan, "Fragmentation of Fluorosulfonyldifluoroacetyl Fluoride Induced by Fluoride Ion", J. of Fluorine Chem., 16, pp. 385-290 (May 1980).

Navarrini et al., "Organic Hypofluorites and Their Role in Industrial Fluorine Chemistry", J. of Fluorine Chem., 95, pp. 27-39 (1999).
Banks et al., "Electrochemical Fluorination (Simons Process) as a Route to Perfluorinated Organic Compounds of Industrial Interest", Preparation, Properties and Industrial Applications of Organofluorine Compounds, John Wiley & Sons, pp. 19-43 (1982).
Hudlicky, "Hydrolytic Removal of Fluorine", Chemistry of Organic Fluorine Compounds, John Wiley & Sons, pp. 273-274 (1976).
Barcina et al., "Oxidation of Fluoroalkenes by Potassium Permanganate", Organo-Fluorine Compounds, vol. E10b, Pt. 1, pp. 691-692 (1999).
Banks et al., "Some Derivatives of Perfluoro-oxdiacetic Acid (Perfluoro-β-oxaglutaric Acid)", J Chem. Soc., (C), pp. 1969-1709 (1969).
European Search Report, Jun. 2005.
Chemical Abstracts, "Manufacture of acyl peroxides", XP-002333403, Database accession No. 1997:286376, 1997.
Chemical Abstracts, "Preparation of perhalo(ethyl 3-butenyl ethers) as intermediates for perfluoro(vinyl 3-butenyl ether", XP-00233404, Database accession No. 1991:206552, 1990.

* cited by examiner

*Primary Examiner*—Rosalynd Keys
(74) *Attorney, Agent, or Firm*—Arent Fox LLP

(57) ABSTRACT

A process for preparing (per)fluorohalogenethers having general formula:

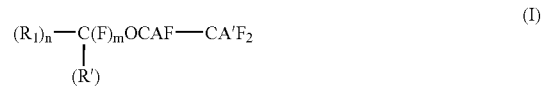

wherein:
A and A', equal to our different from each other, are selected among Cl, Br, H; m=1, 2; n=0, 1; $R_1$ is a fluorinated substituent, preferably perfluorinated, selected from the following groups: $C^1$-$C_{20}$ linear or branched alkylic; $C_3$-$C_7$ cycloalkylic; aromatic, $C_6$-$C_{10}$ arylalkyl; heterocyclic or $C_5$-$C_{10}$-alkylheterocyclic; preferably perfluoroalkyl; R' is as defined in the application;
by reaction of carbonyl compounds having formula:

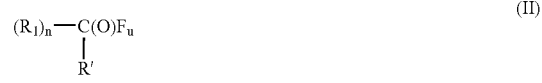

wherein:
$R_1$ and n are as above; u=0, 1; R' is as defined in the application;
in liquid phase, with elemental fluorine and with olefinic compounds of formula:

$$CAF=CA'F_2 \quad (III)$$

wherein A and A' are as above,
at temperatures from −120° C. to −20° C., preferably from −100° C. to −40° C., optionally in the presence of an inert solvent under the reaction conditions.

8 Claims, No Drawings

PROCESS FOR PREPARING FLUOROHALOGENETHERS

The present invention relates to a process for preparing fluorinated vinylethers having a (per)fluoro-alkyl structure.

More specifically the present invention relates to the preparation of fluorohalogenethers having a (per)fluoro-alkyl structure which by dehalogenation or dehydro-halogenation give fluorinated bisvinylethers and/or fluorinated monovinylethers wherein the other end group contains a carbonyl group. The process of the invention brings to obtain fluorohalogenethers having a (per)fluoroalkyl structure with a good selectivity. The fluorinated monovinylethers wherein the other end group contains a carbonyl group are novel.

As known, fluorinated vinylethers form a class of valuable monomers for obtaining various polymers, from fluorinated elastomers to thermoprocessable semicrystalline fluorinated polymers.

Processes for obtaining fluorohalogenethers using the reaction of hypofluorites with olefins are known in the prior art. For the hypofluorite preparation the most known processes use metal fluorides-based catalysts.

In U.S. Pat. No. 4,827,024 it is described the preparation in a continuous way of hypofluorites, by fluorination, in equimolecular amounts, with fluorine of halogenated carbonyl compounds having at least two carbon atoms, in the presence of catalysts formed of CsF, optionally in admixture with metals as, for example, copper. Generally these metals are used, besides as catalyst (CsF) supports, also to make the thermal exchange easier, i.e. to dissipate the heat generated in the hypofluorite synthesis.

The metal support according to the above described prior art must accomplish two main functions: 1) to maintain the catalyst in a form accessible to the reactants, 2) to facilitate the thermal exchange maintaining controllable in the required range the temperature of the catalytic bed. Further and essential feature of the support is the complete inertia towards the reactants and reaction products.

In U.S. Pat. Nos. 4,816,599, 4,801,409 and 4,962,282 hypofluorites are preferably prepared by using an excess of fluorine to completely convert the acylfluoride into hypofluorite so that the acylfluoride concentration on the catalytic bed is very low, since it is known that some acylfluorides give rise to decomposition reactions in the presence of CsF. See for example Carl G. Krespan in Journal of Fluorine Chemistry, 16 (1980) 385-390.

Tests carried out by the Applicant on the processes of the prior art for preparing hypofluorites, by using the above described catalysts, have shown that by using said catalytic systems, both in a discontinuous and continuous way, the catalytic activity is rapidly reduced in the time. The Applicant has found in particular that the activity reduction is very marked, until complete catalyst deactivation, when in the hypofluorite synthesis an excess of fluorine on the stoichiometric value is used, condition indicated as preferred in the described processes of the prior art.

According to the prior art one must therefore operate in excess of fluorine in the hypofluorite synthesis to reduce as much as possible the above inconveniences. By operating under said conditions the prior art catalyst deactivates very rapidly, in about two-three days. With so low durations it is in practice impossible to have available a continuous industrial plant.

Furthermore, in the hypofluorite synthesis processes in a discontinuous way, when the catalytic bed is used in the absence of support, its further use in the reaction for obtaining hypofluorites brings to very low yields and a very quick deactivation is observed.

Processes to obtain fluorinated vinylethers are known in the prior art. U.S. Pat. No. 4,900,872 describes the preparation of perfluorovinylether precursors, by continuous reaction between perfluoroalkyl hypofluorites diluted in an inert solvent and an olefin having formula $CA'F=CA''F$, wherein A and A', equal to or different from each other, are Cl and Br. In the patent it is indicated that said hypofluorites can be directly fed from the reactor wherein their synthesis takes place in gaseous phase, by reaction of fluorine with acylfluoride on catalyst. The obtained products are converted into perfluorovinylethers by dehalogenation with zinc. In this process the drawbacks are those above reported as regards the hypofluorite preparation. In particular the drawback of said processes resides in that one has to synthesize and immediately use the hypofluorites, which, as known, are unstable compounds, in particular when the number of carbon atoms in the hypofluorite perfluoroalkyl chain is higher than or equal to 2. Besides, in the hypofluorite synthesis it is known that a catalyst must be used, with the above drawbacks.

In U.S. Pat. No. 5,225,576 the reaction between hypofluorite and a (per)halo-olefin for preparing (per)haloethers is carried out by flowing a gaseous phase, containing the hypofluorite, in the liquid phase containing the (per)haloolefin maintained at low temperature. To obtain high yields of the sum reaction, it is necessary to work at a low temperature. Under these conditions however a partial hypofluorite condensation can take place before the hypofluorite comes into contact with the olefin. This leads to the hypofluorite decomposition and therefore explosions can be caused. For example the hypofluorite $CF_3CF_2CF_2OF$ having a molecular weight 204 has a boiling point of $-9°$ C. (Journal of fluorine Chemistry, Vol. 95 (1999) 29) and can easily condensate at the temperatures used in the (per)haloether synthesis. At temperatures lower than $-30°$ C. the process of the above patent is applicable only to hypofluorites having a low boiling point, i.e. having 1 or 2 carbon atoms in the chain.

U.S. Pat. No. 4,906,770 describes hypofluorites of formula $Rf^1OCF_2OF$ and $FOCF_2ORf^1OCF_2OF$, wherein $Rf^1$ is a perfluoropolyether radical, even of high molecular weight, and the respective addition products with olefins. The process for preparing said hypofluorites requires a peroxide fluorination with UV light at temperatures in the range from $-60$ to $30°$ C. The reaction times are very long and the conversion into hypofluorite, when it is complete, determines low hypo-fluorite yields. See the Examples. Besides, the use of the UV light is expensive in an industrial process.

U.S. Pat. No. 4,801,409 describes the preparation of bis hypofluorites of general formula $FOCF_2-Rf^3-CF_2OF$ in gaseous phase. $Rf^3$ is a perfluoroalkylene or perfluorooxyalkylene. The only Example of hypofluorite having a number of carbon atoms higher than two is an hypofluorite having three carbon atoms. Tests carried out by the Applicant have shown that with these hypofluorites very low yields of addition to olefins are obtained.

In the prior art the hypofluorite synthesis with a number of carbon atoms higher than two is carried out at temperatures from $0°$ C. to $60°$ C., in particular at $20°$ C. in gaseous phase, to avoid the condensation and thus explosions. Furthermore very high dilutions of the acylfluoride precursor are used. See U.S. Pat. No. 4,801,409.

EP 1,333,020 describes a process having high yields for the synthesis of (per)haloethers obtained from hypofluorites having a number of carbon atoms higher than 2, by using also hypofluorites having a high molecular weight. The (per)haloethers can have (per)fluoroalkyl and oxy(per)-fluoroalkyl chain; besides they can be mono or bifunctional depending on the use of mono or bis-hypofluorite precursors. In the process described in EP 1,333,020, which can be in continuous, semicontinuous or discontinuous, hypofluorites at high concentrations, even without solvent, and catalysts of formula MeFy.zHF for their synthesis from acylfluorides, are used. The drawbacks of this process are the same previously mentioned connected with the catalyst and the hypofluorite use.

The need was felt to have available a process for preparing fluorohalogenethers avoiding the drawbacks of the prior art and characterized at the same time by a good selectivity in the fluorohalogenether synthesis.

An object of the present invention is a process for preparing (per)fluorohalogenethers having general formula:

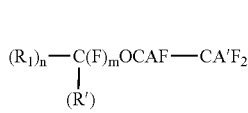   (I)

wherein:

A and A', equal to or different from each other, are selected among Cl, Br and H, with the proviso that A and A' are not contemporaneously equal to H;

m=1, 2;

n=0, 1;

with the proviso that when m=1 then n=1 and when m=2 then n=0;

$R_1$ is a fluorinated substituent, preferably perfluorinated, selected from the following groups:

$C_1$-$C_{20}$ linear or branched alkyl; $C_3$-$C_7$ cycloalkyl; aromatic, $C_6$-$C_{10}$ arylalkyl; $C_5$-$C_{10}$ heterocyclic or alkylheterocyclic; preferably perfluoroalkyl;

when $R_1$ is fluorinated or perfluorinated alkyl or cycloalkyl, it can optionally contain in the chain one or more oxygen atoms;

when $R_1$ is fluorinated it can optionally contain one or more H atoms and/or one or more halogen atoms different from F;

$R'=(R_I)_pT$ wherein:

$R_I$ is a fluorinated or perfluorinated substituent, preferably perfluorinated, selected from the following groups: $C_1$-$C_{20}$ linear or branched alkylene, $C_3$-$C_7$ cycloalkylene;

when $R_I$ is fluorinated it can optionally contain one or more H atoms and/or one or more halogen atoms different from F;

when $R_I$ is perfluorinated it can optionally contain one or more oxygen atoms;

p=0, 1;

T has the following meanings:

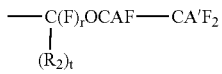

wherein:

A and A' are as above defined;

r=1, 2;

t=0, 1;

with the proviso that when r=1 then t=1 and when r=2 then t=0;

$R_2$ has the $R_1$ meanings and can be equal to or different from $R_1$;

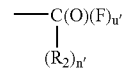

wherein n'=0, 1;

u'=0, 1;

$R_2$ is as above;

with the proviso that when u'=0 then n'=1; when u'=1 then n'=0;

by reaction of carbonyl compounds having formula:

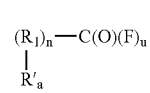   (II)

wherein:

$R_1$ and n are as above;

u=0, 1;

$R'_a=-(R_I)_pQ$ wherein:

$R_1$ and p are as above;

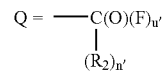

wherein n', u' and $R_2$ are as above; with the proviso that when u=0 then n=1 and when u=1 then n=0; and when u'=0 then n'=1; when u'=1 then n'=0;

in liquid phase, with elemental fluorine and with olefinic compounds of formula:

   (III)

wherein A and A' are as above, at temperatures from −120° C. to −20° C., preferably from −100° C. to −40° C., optionally in the presence of an inert solvent under the reaction conditions.

The fluorine used in the reaction can optionally be diluted with an inert gas such as nitrogen or helium.

The process according to the present invention is carried out in a sole reactor and the reaction can be carried out in a semicontinuous or continuous way.

The semicontinuous process can, for example, be carried out by feeding gaseous fluorine into the reactor containing the carbonyl compounds of formula (II) and the olefinic compounds of formula (III). The molar ratio (II)/(III) can range in a wide range, for example between 0.05 and 10. The fluorine feed is continued until complete olefin conversion. This condition can be easily determined when the exothermy of the reaction is no longer noticed. Indeed by carrying out the reaction of the compounds (II) and (III) for example at −100° C., as soon as the reaction compounds react with the elemental fluorine, there is exothermy and the temperature increases of about 5°-15° C. Therefore the reaction ends when, for example, the compound (III) has been completely consumed. At this point the reactor temperature returns to the initial value.

In the continuous process the gaseous fluorine and the compounds (II) and (III) are fed into the reactor, until reaching the steady state. In practice the reactants are fed into the reactor with fixed flow-rates and the reaction mixture is continuously drawn. The steady state is reached when the concentrations of the three reactants and of the reaction products in the reactor are equal to the concentration of the reactants and the reaction products flowing out from the reactor.

The molar ratios between the reactants are not particularly binding, for example the molar ratio (II)/(III) can range from 0.05 to 10 and $F_2$/(III) from 0.05 to 10.

As solvents in the process of the present invention, compounds liquid and inert, in the above range of temperatures, can be used. Compounds selected, for example, from (per)fluorocarbons, (per)fluoroethers, (per)fluoropolyethers, perfluoroamines, or respective mixtures, can be used. The skilled in the field is able to select in the above classes the compounds to be used as solvents on the basis of their physical properties.

The precursors of the carbonyl compounds of formula (II) can be prepared according to various methods known to the skilled in the field. For example the (per)fluoro-acyl fluorides can be prepared:

by electrochemical fluorination of hydrogenated carboxyl acids (or corresponding esters or acyl chlorides) in anhydrous HF ("Preparation, properties and industrial application of organofluorine compounds" R. E. Banks, ed. 1982, pages 19-43);

by reaction of (per)fluoroakyl iodides with oleum (M. Hudlicky "Chemistry of organic fluorine compounds; a laboratory manual", Ellis Horword Ltd 1976, page 273), by oxidation of fluoroalkenes (Houben Weil vol. E 10b 1999, page 691);

by reaction of (per)fluoroacyl chlorides with NaF (J. Chem Soc. (C), 1969, pages 1706-1709). The (per)fluoroketones as well as the (per)fluoroacyl fluorides can be prepared by disproportionation of (per)fluorocarboxylic esters in the presence of a fluoride ion source (U.S. Pat. No. 5,466,877). Said (per)fluorocarboxylic esters can be prepared by direct fluorination with elemental fluorine of the corresponding hydrogenated or partially fluorinated esters.

The compounds of formula (II) are for example COF—COF, COF—$(CF_2)_2$COF, COF—$(CF_2)_4$COF, COF—$(CF_2)_6$COF, COF—$CF_2OCF_2$—COF, $CF_3$C(O)—C(O)—$CF_3$, $CF_3$C(O)—COF. Preferably COF—COF, COF—$(CF_2)_2$—COF, COF—$(CF_2)_4$COF, COF—$(CF_2)_6$COF, COF—$CF_2OCF_2$—COF are used.

The conversion of the fluorohalogenethers of formula (I) into the corresponding vinylethers with —OCF=$CF_2$ end groups can be carried out by the known dehalogenation and dehydrohalogenation methods of the prior art.

As said, the fluorinated monovinylethers wherein the other end group contains a carbonyl group, obtainable with the invention process, are novel.

The following Examples are given for illustrative and non limitative purposes of the present invention.

EXAMPLES

Example 1

Synthesis of Fluorohalogenethers from Diacyl Fluoride F(O)C—$(CF_2)_6$—COF

A sample of diacylfluoride (4.2 g) F(O)C—$(CF_2)_6$—COF is dissolved in 42 g of $CFCl_3$ (CFC 11). The solution is fed into a 50 $cm^3$ glass reactor equipped with stirrer, bubbling inlets for the fluorine and CFC 1112 (CFCl=CFCl) feeding. The reaction is carried out at −40° C. by feeding 1.7 Nl/h of fluorine diluted with 4.2 Nl/h of helium (molar ratio helium/fluorine=2.5/1) and CFC 1112 with flow rate equal to 1.6 Nl/h, for 90 minutes.

The material balance is 96%. The reaction raw product is distilled at 40° C. at the head. The heavy fraction and the light fraction are characterized by gaschromatography. The light fraction contains CFC 114, CFC 11 and unreacted F(O)C—(—$CF_2)_6$—COF. From the analyses it is calculated a conversion of the —C(O)F end groups of 33.9% with a selectivity to —O—CFCl—$CF_2$Cl end groups of 49.0%, so divided:

36.1% to the —OCFC$_1$—$CF_2$Cl end groups of the mono-addition compound of formula $CF_2$Cl—CFCl—O—$(CF_2)_7$—COF;

8.6% to the —OCFC$_1$—$CF_2$Cl end groups of the bis adduct of formula $CF_2$Cl—CFCl—O—$(CF_2)_8$—O—CFC$_1$—$CF_2$Cl;

4.3% to the —OCFC$_1$—$CF_2$Cl end groups of the compound of formula $C_7F_{15}$—O—CFC$_1$—$CF_2$Cl.

The conversion of F(O)C—$(CF_2)_6$—COF is 51.3%.

The selectivity to the mono addition compound $CF_2$Cl—CFCl—O—$(CF_2)_7$—COF with respect to F(O)C—$(CF_2)_6$—COF is 47.7% and that of the bis adduct $CF_2$Cl—CFCl—O—$(CF_2)_8$—O—CFC$_1$—$CF_2$Cl is 5.6%.

Example 2

Synthesis of Fluorohalogenethers from Diacyl Fluoride F(O)C—$(CF_2)_6$—COF

A sample of diacylfluoride (5.0 g) having structure F(O)C—$(CF_2)_6$—COF is dissolved in 19.8 g of $CFCl_3$ (CFC 11). The solution is fed into a 50 $cm^3$ glass reactor equipped with stirrer and bubbling inlets for the fluorine and CFC 1112 (CFCl=CFCl) feeding. The reaction is carried out at −40° C. by feeding 1.7 Nl/h of fluorine diluted with 4.2 Nl/h of helium (molar ratio helium/fluorine=2.5/1) and CFC 1112 with flow rate equal to 1.6 Nl/h, for 180 minutes.

The material balance is 97%. The reaction raw product is distilled at 40° C. at the head. The heavy fraction and the light fraction are characterized by gaschromatography. The light fraction contains CFC 114, CFC 11 and unreacted F(O)C—(—$CF_2)_6$—COF. From the analyses it is calculated a conversion of the —C(O)F end groups of 96.9% with a selectivity to —O—CFCl—$CF_2$Cl end groups of 52.0%, so divided:

3.1% to the —OCFC$_1$—$CF_2$Cl end groups of the mono-addition compound of formula $CF_2$Cl—CFCl—O—$(CF_2)_7$—COF;

48.7% to the —OCFCl—$CF_2$Cl end groups of the bis adduct of formula $CF_2$Cl—CFCl—O—$(CF_2)_8$O—CFC$_1$—$CF_2$Cl;

0.2% to the —OCFCl—$CF_2$Cl end groups of the compound of formula $C_7F_{15}$—O—CFC$_1$—$CF_2$Cl.

The conversion of F(O)C—$(CF_2)_6$—COF is 98%. The selectivity to the mono addition compound $CF_2$Cl—CFCl—O—$(CF_2)_7$—COF with respect to F(O)C—$(CF_2)_6$—COF is 6.2% and that of the bis adduct $CF_2$Cl—CFCl—O—$(CF_2)_8$—O—CFCl—$CF_2$Cl is 48.3%.

The invention claimed is:

1. A process to prepare (per)fluorohalogenethers having general formula:

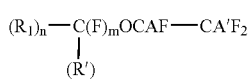 (I)

wherein:
A and A', equal to or different from each other, are selected among Cl, Br and H, with the proviso that A and A' are not contemporaneously equal to H;
m=1, 2;
n=0, 1;
with the proviso that when m=1, n=1 and when m=2, n=0;
$R_1$ is a fluorinated substituent selected from the following groups: $C_1$-$C_{20}$ linear or branched alkyl; $C_3$-$C_7$ cycloalkyl; aromatic; $C_6$-$C_{10}$ arylalkyl; $C_5$-$C_{10}$ heterocyclic or alkylheterocyclic;
when $R_1$ is fluorinated or perfluorinated alkyl or cycloalkyl, it can optionally contain in the chain one or more oxygen atoms;
when $R_1$ is fluorinated it can optionally contain one or more H atoms and/or one or more halogen atoms different from F;
$R'=(R_I)_pT$ wherein:
$R_I$ is a fluorinated or perfluorinated substituent selected from the following groups: $C_1$-$C_{20}$ linear or branched alkylene, $C_3$-$C_7$ cycloalkylene;
when $R_I$ is fluorinated it can optionally contain one or more H atoms and/or one or more halogen atoms different from F;
when $R_1$ is perfluorinated it can optionally contain one or more oxygen atoms;
p =0, 1;
T has the following meanings:

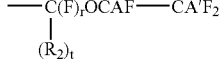

wherein:
A and A' are as above;
r=1, 2;
t=0, 1;
with the proviso that when r=1 then t=1 and when r=2 then t=0;
$R_2$ has the $R_1$ meanings and can be equal to or different from $R_1$;

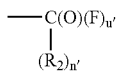

wherein
n'=0, 1;
u'=0, 1;
$R_2$ is as above;
with the proviso that when u=0 then n'=1; when u'=1 then n'=0;

by reaction of carbonyl compounds having formula:

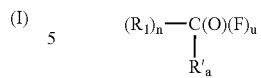 (II)

wherein:
$R_1$ and n are as above;
u=0, 1;
$R'_a=-(R_I)_pQ$
wherein:
$R_I$ and p are as above;

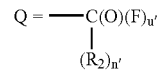

wherein n', u' and $R_2$ are as above;
with the proviso that when u=0 then n=1 and when u=1 then n=0; and when u'=0 then n'=1; when u'=1 then n'=0;
in liquid phase, with elemental fluorine and with olefinic compounds of formula:

CAF=CA'F    (III)

wherein A and A' are as above, at temperatures from −120° C. to −20° C., optionally in the presence of an inert solvent under the reaction conditions.

2. A process according to claim 1, wherein the fluorine used in the reaction is diluted with an inert gas.

3. A process according to claim 1, carried out in a sole reactor in a semicontinuous or continuous way.

4. A process according to claim 3 carried out in a semicontinuous way, wherein the molar ratio between the carbonyl compounds of formula (II)/olefinic compounds of formula (III) ranges from 0.05 to 10.

5. A process according to claim 3, carried out in a continuous way, wherein the molar ratio (II)/(III) ranges from 0.05 to 10 and the molar ratio $F_2$/(III) from 0.05 to 10.

6. A process according to claim 1, wherein as solvents compounds selected from (per)fluorocarbons, (per)fluoroethers, (per)fluoropolyethers, perfluoroamines, or their respective mixtures, are used.

7. A process according to claim 1, wherein the compounds of formula (II) are selected from COF—COF, COF—$(CF_2)_2$COF, COF—$(CF_2)_4$COF, COF—$(CF_2)_6$COF, COF—$CF_2$OCF_2$—COF, $CF_3C(O)$—C(O) —$CF_3$, and $CF_3C(O)$—COF.

8. A process according to claim 1, wherein the fluorohalogenethers of formula (I) are converted into the corresponding vinylethers with —OCF=$CF_2$ end groups by dehalogenation or dehydrohalogenation methods.

* * * * *